(12) United States Patent
Schwirten et al.

(10) Patent No.: US 7,183,233 B2
(45) Date of Patent: Feb. 27, 2007

(54) METHOD FOR SEPARATING AN ESTERIFICATION CATALYST

(75) Inventors: Kurt Schwirten, Frankenthal (DE); Walter Disteldorf, Wachenheim (DE); Günther Golfier, Frankenthal (DE); Jarren Peters, Mannheim (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 93 days.

(21) Appl. No.: 10/523,284

(22) PCT Filed: Jul. 23, 2003

(86) PCT No.: PCT/EP03/08035

§ 371 (c)(1), (2), (4) Date: Feb. 3, 2005

(87) PCT Pub. No.: WO2004/018406

PCT Pub. Date: Mar. 4, 2004

(65) Prior Publication Data

US 2005/0240053 A1    Oct. 27, 2005

(30) Foreign Application Priority Data

Aug. 8, 2002   (DE)   .............................. 102 36 279

(51) Int. Cl.
*C07C 67/48*   (2006.01)
*B01J 20/31*   (2006.01)

(52) U.S. Cl. .......................................... 502/25; 560/191
(58) Field of Classification Search ................ 560/190; 502/25

See application file for complete search history.

(56) References Cited

U.S. PATENT DOCUMENTS 4,241,216 A * 12/1980 Bergman et al. ............... 560/99
5,750,739 A *  5/1998 Isozaki et al. ............... 549/515

FOREIGN PATENT DOCUMENTS

| CS | 274 812   | 11/1991 |
| DE | 1 945 359 | 3/1971  |
| DE | 2 318 657 | 10/1974 |
| DE | 26 12 355 | 10/1977 |
| DE | 197 21 347| 11/1998 |
| GB | 1030214   | 5/1966  |

* cited by examiner

*Primary Examiner*—Thurman K. Page
*Assistant Examiner*—Karl J. Puttlitz
(74) *Attorney, Agent, or Firm*—Connolly Bove Lodge & Hutz, LLP

(57) ABSTRACT

Process for removal of the esterification catalyst by separation from a crude plasticizer ester obtained by reacting a dicarboxylic acid with $C_8$–$C_{13}$ alcohols, by treating the crude ester with an aqueous alkali solution in the range from 10 to 100° C. and then separating the aqueous alkaline phase comprising the hydrolyzed esterification catalyst by gravitational phase separation, by treating the crude ester, prior to or during the phase separation, with a salt of a di- or polyvalent metal, or with a mixture of these salts.

15 Claims, No Drawings

METHOD FOR SEPARATING AN ESTERIFICATION CATALYST

RELATED APPLICATIONS

This application is a national stage application (under 35 U.S.C. 371) of PCT/EP2003/008035 filed on Jul. 23, 2003 which claims benefit to German application Serial No. DE 102 36 279.3 filed Aug. 8, 2002.

The present invention relates to a process for removal of the esterification catalyst by separation from a crude plasticizer ester obtained by reacting a dicarboxylic acid with $C_8$–$C_{13}$ alcohols, by treating the crude ester with an aqueous alkali solution in the range from 10 to 100° C. and then separating the aqueous alkaline phase comprising the hydrolyzed esterification catalyst by gravitational phase separation.

Phthalic diesters and adipic diesters are important plasticizers for plastics, in particular PVC. When these diesters are produced industrially, the usual method is to react phthalic anhydride or adipic acid with approximately twice the molar amount of an alcohol in the presence of an esterification catalyst. Important members of the resultant class of phthalic diesters and adipic diesters are the dialkyl esters, derived from the corresponding alcohols, such as octanols or nonanols. The esterification catalysts mostly used nowadays are Lewis-acid salts of elements of the 4th main group or the 4th transition group of the Periodic Table of the Elements.

At the end of the esterification reaction, the esterification catalyst is normally destroyed by adding alkali. Practical considerations means that the materials mostly used for this purpose are aqueous solutions of an alkali metal hydroxide or of an alkali metal carbonate. The hydrolysis products of the esterification catalyst are mainly in the aqueous phase after catalyst destruction, and that phase is then removed by separation.

However, a difficulty mostly arising with the separation of organic product phase and alkaline aqueous phase under practical conditions is that an emulsion layer forms between the two phases to be separated after catalyst destruction.

It has now been found that this emulsion layer comprises hydrolysis products of the catalyst, and also alkali metal salts of half-esters made from one mol of dicarboxylic acid and one mol of esterification alcohol (the term "half-ester" being used for these below). The emulsion layer frequently also comprises considerable amounts of diester.

The half-esters derive firstly from incomplete conversion of the monoester by the esterification alcohol. Secondly, they can also be produced from diester by alkaline hydrolysis during the destruction of the esterification catalyst by alkali.

These emulsions cannot generally be broken in conventional separators using prolonged residence times. A consequence of this is that the emulsions often pass to some extent into the organic phase during phase separation and, when this phase is worked up, cause undesirable deposits in the downstream sections of the plasticizer-production plant. Some of the emulsion can also be separated out with the aqueous phase, causing product losses.

It has therefore been desirable to find a process for "breaking" these emulsions prior to phase separation.

The use of chemical means for this purpose is known to the skilled worker.

For example, DE-A 23 18 657 describes the two-stage destruction of an oil-in-water emulsion by using $FeCl_3$ or $AlCl_3$ to adjust to a pH of from 2 to 3. Immediately following this, NaOH or $Ca(OH)_2$ is used for neutralization.

The Czechs patent CS 274812 also proposes a two-stage process, in which the emulsion is first acidified and then treated with a polyvalent salt, such as $Al_2(SO_4)_3$, $Fe_2(SO_4)_3$ or $FeCl_3$.

A precondition for each of these known processes is therefore that the emulsion to be broken has a pH markedly below 7 (acid range).

When applied to the present technical problem, namely the destruction of an emulsion at the interface between an organic product phase and an alkaline aqueous phase of a crude esterification product, these known processes are inconvenient and not cost-effective.

It is an object of the present invention, therefore, to provide a process which is simpler and more cost-effective to carry out for the destruction of these emulsions arising during the alkaline aqueous hydrolysis of the catalysts in the above mentioned preparation processes for dicarboxylic diesters.

We have found that this object is achieved by means of a process for removal of the esterification catalyst by separation from a crude plasticizer ester obtained by reacting a dicarboxylic acid with $C_8$–$C_{13}$ alcohols, by treating the crude ester with an aqueous alkali solution in the range from 10 to 100° C. and then separating the aqueous alkaline phase comprising the hydrolyzed esterification catalyst by gravitational phase separation, which comprises treating the crude ester, prior to or during the phase separation, with a salt of a di- or polyvalent metal, or with a mixture of these salts.

The dicarboxylic acids used may be aromatic or aliphatic organic dicarboxylic acids preferably having from 3 to 12 carbon atoms. Particular preference is given to dicarboxylic acids of this type having from 6 to 8 carbon atoms, such as adipic acid and phthalic acid. Instead of the dicarboxylic acids, it is also possible to use their derivatives which are generally more reactive in esterification reactions, for example phthalic anhydride in the case of phthalic acid, or the acid dichlorides.

The esterification alcohols preferably used are monoalcohols having from 6 to 13 carbon atoms. Particular preference is given to branched or unbranched monoalcohols, or mixtures of branched and unbranched monoalcohols, having from 8 to 11 carbon atoms.

The process of the invention is particularly suitable for the destruction of emulsions arising during the preparation of di-$C_8$ phthalates, di-$C_9$ phthalates, di-$C_{10}$ phthalates, di-$C_8$ adipates, di-$C_9$ adipates, and di-$C_{10}$ adipates.

As esterification catalyst, preference is given to a Lewis-acid compound of an element of the 4th main group or of the 4th transition group of the Periodic Table of the Elements.

Preferred esterification catalyst metals are tin, antimony, titanium, or zirconium, titanium being particularly preferred.

Preferred esterification catalysts are the halides, alkoxylates, and alkoxycarbonylates of the esterification-catalyst metals, for example $TiCl_4$, $ZrCl_2(O\text{-ethyl})_2$, $ZrOCl_2$; particular preference is given to the titanium alkoxylates, and in particular $Ti(O\text{-ethyl})_4$, $Ti(O\text{-isopropyl})_4$, $Ti(O\text{-isobutyl})_4$.

The amount used of the esterification catalyst, based on the dicarboxylic acid to be esterified or, where appropriate, on the derivative of the dicarboxylic acid, is generally from 0.001 to 0.8% by weight, preferably from 0.01 to 0.08% by weight.

Other aspects of the preparation of the dicarboxylic diesters using these esterification catalysts are quite familiar to the person skilled in the art (cf., for example, DE-A 1 945 359), and it is therefore unnecessary to give further details in this connection.

Completion of the reaction of the dicarboxylic acid with the esterification alcohol in the presence of the esterification catalyst generally gives a homogeneous solution of the esterification catalyst in the crude product mixture, mainly composed of diester.

To destroy the esterification catalyst, the product mixture is generally treated with a from 2 to 10% strength by weight aqueous alkali solution, such as sodium hydroxide solution, or with an aqueous solution of potassium carbonate and water. The method of operation here is normally that the final phase ratio of the aqueous phase to the organic phase is in the range from 0.1:1 to 10:1 parts by weight.

Based on a volume of 1 liter of the aqueous phase, from 0.05 to 30 nmol of a salt of a di- or polyvalent metal or of a mixture of these salts is added to the resultant two-phase system composed of organic product phase and aqueous phase.

Preferred salts used for the process of the invention are: halides, sulfates, mixed halide sulfates, and ternary alkali metal halides/sulfates of iron, aluminum, and calcium, for example sulfates such as aluminum sulfates, e.g. $Al_2(SO_4)_3$, iron sulfate, e.g. $Fe_2(SO_4)_3$, chlorides such as aluminum chloride, iron(III) chloride, potassium aluminum sulfates such as $KAl(SO_4)_2$, calcium salts such as calcium oxide and calcium chloride. Particular preference is given to calcium salts and aluminum salts, and among these very particular preference is given to the aluminum salts.

The form in which the salt or the mixture of salts is added may be that of a solution, preferably in water, or a solid.

In one preferred embodiment of the process of the invention, the salt or the mixture of the salts is added to the crude ester during the alkali treatment and/or during any washing carried out.

The metal salt solution reaction is generally carried out at from 10 to 120° C., preferably from 40 to 90° C., and at a pressure of from 0.5 to 4 bar, preferably at atmospheric pressure.

The process of the invention may be carried out continuously or batchwise, and it is generally particularly cost-effective here to operate continuously where the destruction of the esterification catalyst is also carried out continuously. Similar considerations apply to batchwise operation.

Mixing apparatus preferably used are stirred vessels equipped with drive systems having stepless control, for example blade stirrers, which give homogeneous mixing.

The average residence time in the mixing apparatus is from 0.5 to 45 minutes, preferably from 10 to 20 minutes.

Prior to the gravitational phase separation, the crude ester preferably has from 0.1 to 5% by weight content of monosalt of dicarboxylic half-ester.

The subsequent gravitational phase separation may use vertical phase separators, since the removal of the solids here (e.g. titanium hydroxide) by separation is particularly simple. However, horizontal phase separators may also be used, since the titanium hydroxides sediment rapidly and completely in the aqueous phase, normally without forming any solids-containing intermediate layer out of crude ester, aqueous phase, and titanium hydroxide particles which is difficult to separate.

The phase separation times for the liquid/liquid separation and for the solid/liquid separation are generally in the range from 5 to 30 minutes.

The organic phase removed by separation and substantially composed of the diester and unreacted esterification alcohol is then further purified in a manner known per se to the skilled worker, for example by stripping.

The aqueous phase removed by separation normally comprises most of the monosalt of dicarboxylic half-ester.

One advantage of the process of the invention is that the phase separation generally takes place rapidly and without disruption (without formation of solids-containing intermediate layers and emulsions).

A particular advantage is that the plasticizer esters are free from solids when they pass into the downstream stages of the process. This can give an increase in the operating times of the apparatus used, by a factor of from 10 to 20.

The economic advantages of working the process of the invention on an industrial scale are an increase in capacity in the stages of the process for crude ester treatment, and also an increase in availability and operating reliability. The reduction in the number of purification phases considerably reduces the maintenance costs for the plants used and cuts plasticizer ester losses.

EXAMPLES

Example 1

180 g of crude diisononyl phthalate (prepared as in DE-A 197 21 347) were thoroughly mixed for 5 minutes in a separating funnel with 20 g of water and 0.4% by weight, based on the mixture, of the monosodium salt of monoisononyl phthalate. The resultant mixture had a milky cloudiness, and there was no remaining detectable phase boundary. 3% by weight, based on the mixture, of a 0.5 millimolar aqueous solution of aluminum sulfate were then added to the mixture, and the entire mixture was again vigorously mixed. After standing for ten minutes, there was a clearly discernible phase boundary between the two different cloudy phases.

Example 2

A stable emulsion from a production plant with 24% by weight of water of pH 9.8, 2.5% by weight of isononanol, and 73% by weight of diisononyl phthalate, and also 0.5% by weight of monosodium salt of monoisononyl phthalate, was treated with 8% by weight, based on the mixture, of a 0.5 millimolar aqueous solution of aluminum sulfate, and vigorously mixed. After standing for ten minutes, a phase boundary was clearly discernible between the two different phases.

Example 3

Each of three shaking funnels (shaking funnels 1, 2 and 3) was charged with 25 ml of water and 250 g of diisononyl phthalate, and 0.2 g of the monosodium salt of monononyl phthalate was added to each shaking funnel. All three of the shaking funnels were then shaken vigorously. There was then no remaining phase boundary, and in all three cases the product was a stable emulsion. The subsequent procedure was as follows:

Shaking funnel 1: After 1 h 30 min, a white emulsion remained, but about 5 ml of aqueous phase had separated out at the bottom.

Shaking funnel 2: 5 ml of a 10 millimolar calcium chloride solution were added, and the contents of the shaking funnel were again mixed. After 15 min, relatively large droplets formed toward the based. After 1 h, 30 ml of aqueous phase had separated out. Above the phase boundary there was a white non-transparent layer of thickness from 8–10 mm, while the rest of the organic phase was transparent, although cloudy. After 1 h 30 min, no further change was detectable.

Shaking funnel 3: 30 ml of a 10 millimolar calcium chloride solution were added and the contents of the shaking funnel were again mixed. After 15 min, a clear phase boundary was detectable. After 30 min, 55 ml of aqueous phase had separated out. There was a sharp phase boundary—without any sign of emulsion.

We claim:

1. A process for removal of an esterification catalyst by separation from a crude plasticizer ester obtained by reacting a dicarboxylic acid with a $C_8$–$C_{13}$ alcohol, by treating the crude ester with an aqueous alkali solution in the range from 10 to 100° C. and then separating the aqueous alkaline phase comprising the hydrolyzed esterification catalyst by gravitational phase separation, which comprises treating the crude ester with a salt of a divalent metal or a polyvalent metal or mixtures thereof prior to or during the phase separation.

2. A process as claimed in claim 1, wherein the esterification catalyst used comprises a Lewis-acid compound of an element of the 4th main group or of the 4th transition group of the Periodic Table of the Elements.

3. A process as claimed in claim 1, wherein the esterification catalyst used comprises a compound of titanium.

4. A process as claimed in claim 1, wherein, prior to the gravitational phase separation, the crude ester has a content of from 0.1 to 5% by weight of monosalt of dicarboxylic half-ester.

5. A process as claimed in claim 1, wherein the salt used of a divalent metal or a polyvalent metal comprises a calcium salt or an aluminum salt.

6. A process as claimed in claim 5, wherein use is made of an aluminum salt.

7. A process as claimed in claim 6, wherein the amount of aluminum salt used is from 0.05 to 30 mmol per liter of the aqueous alkaline phase.

8. A process as claimed in claim 2, wherein the esterification catalyst used comprises a compound of titanium.

9. A process as claimed in claim 8, wherein, prior to the gravitational phase separation, the crude ester has a content of from 0.1 to 5% by weight of monosalt of dicarboxylic half-ester.

10. A process as claimed in claim 9, wherein the salt used of a divalent metal or a polyvalent metal comprises a calcium salt or an aluminum salt.

11. A process as claimed in claim 10, wherein use is made of an aluminum salt.

12. A process as claimed in claim 11, wherein the amount of aluminum salt used is from 0.05 to 30 mmol per liter of the aqueous alkaline phase.

13. A process as claimed in claim 11, wherein the crude plasticizer ester is obtained by reacting a dicarboxylic acid with a $C_8$–$C_{11}$ alcohol.

14. A process as claimed in claim 1, wherein the esterification catalyst used comprises titanium alkoxylates.

15. A process as claimed in claim 1, wherein the esterification catalyst is $Ti(O\text{-ethyl})_4$, $Ti(O\text{-isopropyl})_4$ or $Ti(O\text{-isobutyl})_4$.

* * * * *